United States Patent [19]

Hooper et al.

[11] 4,278,658
[45] Jul. 14, 1981

[54] DEODORANT COMPOSITION

[75] Inventors: David C. Hooper, Ashford; George A. Johnson; Donald Peter, both of Wirral, all of England

[73] Assignee: Lever Brothers Company, New York, N.Y.

[21] Appl. No.: 3,318

[22] Filed: Jan. 15, 1979

[30] Foreign Application Priority Data

Jan. 13, 1978 [GB] United Kingdom ................ 1479/78
May 16, 1978 [GB] United Kingdom .............. 19842/78

[51] Int. Cl.³ .............................................. A61K 7/32
[52] U.S. Cl. ........................................ 424/65; 8/161; 252/522 R; 424/47; 424/59; 424/69; 424/76; 424/357; 424/358
[58] Field of Search ..................... 424/65, 47, 168, 69

[56] References Cited

U.S. PATENT DOCUMENTS

| | | | |
|---|---|---|---|
| 1,545,931 | 7/1925 | Weeks | 424/65 |
| 1,813,004 | 7/1931 | Weber | 424/65 |
| 2,033,758 | 3/1936 | Cronan et al. | 424/65 X |
| 2,131,235 | 9/1938 | Randall et al. | 424/65 |
| 2,875,131 | 2/1959 | Carpenter et al. | 252/522 |
| 3,091,511 | 5/1963 | Calhoun | 424/65 X |
| 3,166,576 | 1/1965 | Markus | 424/65 |
| 3,172,817 | 3/1965 | Leupold et al. | 424/65 |
| 3,395,214 | 7/1968 | Mummert | 424/65 X |
| 3,493,650 | 2/1970 | Dunkel | 424/65 |
| 3,647,880 | 3/1972 | Blumenthal | 424/65 |

FOREIGN PATENT DOCUMENTS

| | | | |
|---|---|---|---|
| 7604601 | 8/1977 | Brazil . | |
| 2351927 | 4/1975 | Fed. Rep. of Germany | 424/65 |
| 2709267 | 9/1977 | Fed. Rep. of Germany | 424/65 |
| 63749 | 10/1955 | France | 424/65 |
| 8299M | 12/1970 | France | 424/65 |
| 2275193 | 1/1976 | France | 424/65 |
| 550930 | 11/1956 | Italy | 424/65 |
| 52650 | 7/1965 | Norway | 424/65 |
| 425059 | 3/1935 | United Kingdom | 424/65 |
| 977570 | 12/1964 | United Kingdom | 424/65 |
| 1282889 | 7/1972 | United Kingdom | 424/65 |
| 507323 | 4/1976 | U.S.S.R. | 424/65 |

OTHER PUBLICATIONS

Klarmann, The Journal of the Soc. of Cosm. Chemists, 3/1956, vol. 7, No. 2, pp. 85–105.
Ikai, Journal of Investigative Dermatology, 12/1954, vol. 23, No. 6, pp. 411–422.
Drug & Cosmetic Industry, 4/1969, vol. 104, No. 4, pp. 56, 58, 60, 62 & 151–153.
Brevet Special de Medicament, No. 782M, Beiersdorf.
Winter, Handbuch der Gesamten Parfumerie und Kosmetik, 2/1956, pp. 329–414, 470–472.

*Primary Examiner*—Dale R. Ore
*Attorney, Agent, or Firm*—James J. Farrell; Melvin H. Kurtz; Irving N. Feit

[57] ABSTRACT

A deodorant skin treatment product comprises a deodorizing amount of a deodorant composition and a cosmetically acceptable vehicle for the composition other than soap or non-soap detergent. The product can be applied to the skin in order to provide prolonged protection against the development of body malodor.

12 Claims, No Drawings

DEODORANT COMPOSITION

The invention relates to deodorising products for personal use where malodour presents a problem, particularly for application to the skin or hair.

It has long been realised that malodour originating from the human body can constitute an unpleasant experience, and that benefit can be obtained by preventing the development of malodours or by masking or otherwise obliterating malodours when they already exist.

As a means for solving this problem, it is recognised that perfumes have been used as odour maskants since ancient times, and that perfumes have for this reason been incorporated into all manner of consumer products for application to the skin or hair.

It is, however, recognised that the use of perfumes in this manner has its limitations, in that the duration of effectiveness can be relatively short-lived, or that offensive malodours are only partially masked.

It has now been discovered that certain mixtures of substances (some of which can be perfumery materials), hereinafter referred to as "deodorant compositions", when incorporated into products for application to the skin or hair, can provide a more effective means for preventing malodour development or for reducing the perception of malodours which are already present. It is apparent that this effect is not solely one of odour masking, since in many instances there is no detectable fragrance remaining after application of these compositions. Accordingly, the use of deodorant compositions in deodorant products represents a new operative principle.

In the course of attempts to characterise this new principle, many hundreds of substances or blends of substances have been screened for evidence of their deodorant activity.

DEFINITION OF THE INVENTION

In its widest aspect, the invention provides a deodorant skin treatment product comprising from 0.01 to 20% by weight of a deodorant composition and up to 99.99% by weight of a cosmetically acceptable vehicle for the composition, the deodorant composition comprising from 45 to 100% by weight of deodorant components, said components having a lipoxidase-inhibiting capacity of at least 50% or a Raoult Variance Ratio of at least 1.1, said components being classified into six classes consisting of:
  Class 1: phenolic substances
  Class 2: essential oils, extracts, resins and synthetic oils
  Class 3: aldehydes and ketones
  Class 4: polycyclic compounds
  Class 5: esters
  Class 6: alcohols provided that where a component can be classified into more than one class it is placed in the lower or lowest numbered class: said components being selected so that:
  (a) the deodorant composition contains at least five components of which at least one must be selected from each of class 1, class 2 and class 4;
  (b) the deodorant composition contains components from at least 4 of the 6 classes; and
  (c) any component present in the deodorant composition at a concentration of less than 0.5% by weight of said composition is eliminated from the requirements of (a) and (b).

The invention also provides a process for preparing a deodorant skin treatment product which process comprises mixing a deodorant composition as herein defined with a vehicle for the composition to provide a deodorant skin treatment product.

The invention furthermore provides a method for suppressing human body malodour which comprises applying to the human skin in the region of apocrine sweat glands an effective amount of the deodorant skin treatment product as herein defined.

It is a preferred property of the deodorant skin treatment product of the invention that it should comprise a deodorant composition which satisfies a deodorancy test when applied to the skin of human subjects. The average amount by which body malodour should be reduced is expressed in terms of the deodorant value of the deodorant composition contained in the skin treatment product. Products of the invention accordingly preferably comprise a deodorant composition having a deodorant value of from 0.50 to 3.5. Products in which the deodorant composition has a deodorant value of below 0.50 are outside the scope of this invention and are considered to be incapable of reducing body malodour to a significant extent.

THE DEODORANT VALUE TEST

In this test the deodorant value of a deodorant composition is measured by assessing its effectiveness, when contained in a standard soap bar at a standard concentration, in reducing body malodour when the standard soap bar is used to wash the axillae (armpits) of a panel of human subjects.

The choice of a soap base is not critical to the performance of the test but as illustrative of the conduct of the test in this respect the procedure followed in the preparation of the base employed in many of the tests referred to later in this specification is included in the description of the test.

Standard soap bars are prepared as follows, all amounts given being by weight.

As soap base there is used a neutral wet sodium soap containing 63% of total fatty matter of which 82% is tallow fatty acid and 18% is coconut oil fatty acid. To a homogeneous mixture of 9000 parts of this soap base and 340 parts of free coconut oil fatty acid at 80° C. are added with mixing, 9.4 parts of a 20% aqueous solution of tetrasodium ethylenediamine tetraacetate, 2.2 parts of a 60% aqueous solution of 1-hydroxy-ethane-1,1-diphosphonic acid and 7.2 parts of butylated hydroxy toluene (BHT) antioxidant dissolved in a little methylated spirits and the temperature of the mass is raised to 140° C. under superatmospheric pressure. The mass is then sprayed at about 30 mm of mercury, to produce a dried soap composition which is collected and extruded at 30° C. as noodles of about 12% moisture content.

9,770 parts of the soap noodles thus obtained are mixed at ambient temperature with 150 parts of the deodorant composition to be tested, together with 30 parts of a titanium dioxide opacifier and 50 parts of a colourant suspension. The resulting mixture is milled and plodded in conventional equipment, cut into billets and stamped into bars. The deodorant composition to be tested is therefore present at the standard level of 1.5%. These bars are described as 80/20/5 soap base and consist of 80 parts tallow soap and 20 parts coconut soap, 5 parts of this soap mixture being free fatty acids expressed as coconut oil fatty acid.

Control soap bars are prepared in a similar manner except that the deodorant composition is omitted. In other respects, the control bar should only contain those additives conventionally present in personal washing products and for the purpose in the amount conventionally used in the art. For example, it is permissible as indicated in the foregoing description to include antioxidants in the control bar, but these should be present only in the amount required to stabilise the soap base.

The test is conducted as follows:

A team of 3 Caucasian female assessors of age within the range of from 20 to 40 years is selected for olfactory evaluation on the basis that each is able to rank correctly the odour levels of the series of aqueous isovaleric acid solutions listed in Table 1 below, and each is able to detect the reduction in body odour following application to the axillae of human subjects of soap containing 2% germicides, according to the producedure described in Whitehouse and Carter, Proc. Scientific Section of the Toilet Goods Association, 48, 31, (1967).

A panel of 50 human subjects for use in the test is assembled from Caucasian male subjects of age within the range of from 20 to 55 years. By screening, subjects are chosen who develop axilliary body malodour that is not unusually strong and who do not develop a stronger body malodour in one axilla compared with the other. Subjects who develop unusually strong body malodour, for example due to a diet including curry or garlic, are not selected for the panel.

For two weeks before the start of a test, the panel subjects are assigned a non-deodorant soap bar for exclusive use of bathing and are denied the use of any type of deodorant or antiperspirant. At the end of this period, the 50 subjects are randomly divided into two groups of 25. The control soap bars are then applied to the left axillae of the first group and the right axillae of the second, and the test soap bars are applied to the right axillae of the first group and the left axillae of the second.

The soap bars are applied by a technician using a standard technique in which a wet flannel is soaped with the soap bar for 15 seconds, the axilla is washed with the soaped flannel for 30 seconds, then wiped with a water rinsed flannel and dried with a clean towel. Each subject then puts on a freshly laundered shirt, and 5 hours after application the odour intensity of each subject is assessed, the left axilla of each subject being assessed before the right. The application and assessment are carried out on each of four successive days.

The odour intensity is evaluated by all three assessors who, operating without knowledge of the soap bars used for each subject or the result of evaluation of their follow-assessors, sniff each axilla and assign a score corresponding to the strength of the odour on a scale from 0 to 5, with 0 corresponding to no odour and 5 representing very strong odour. Before evaluation each subject stands with his arms against his side: he then raises one arm straight overhead, flattening the axilla vault and making it possible for the assessor's nose to be brought close to the skin, the assessor makes an evaluation and the procedure is repeated with the other axilla.

Standard aqueous solutions of isovaleric acid which correspond to each of the scores, 1,2,3,4 and 5 are provided for reference to assist the assessors in the evaluation. These are shown in Table 1 below.

TABLE 1

| Score | Odour Level | Concentrations of aqueous solution of isovaleric acid (ml/l) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very strong | 3.57 |

The scores recorded by each assessor for each soap bar are averaged and the average score of the test soap bars deducted from the average score of the control soap bars to give the deodorant value of the deodorant composition present in the test soap bars.

As a check that the selection of panel subjects is satisfactory for operation of the test, the average score with the control soap bars should be between 2.5 and 3.5.

More generally, deodorant values can be determined at other deodorant composition concentrations or with detergent products other than the standard soap bar using a test similar to the test described above.

Although the invention in its widest aspect provides deodorant skin treatment products comprising deodorant compositions having a deodorant value of from 0.50 to 3.5, preferred deodorant skin treatment products are those comprising deodorant compositions which have a deodorant value of at least 0.60, or 0.70, or 0.80, or 0.90, or 1.00, 1.20, the higher the minimum value, the more effective is the product as a deodorant skin treatment product as recorded by the assessors in the deodorant value test. It has also been noted that consumers, who are not trained assessors, can detect by self-assessment a noticeable reduction in body malodour where the deodorant value is at least 0.70, the higher the deodorant value above this figure, the more noticeable is the deodorant effect.

THE DEODORANT COMPOSITION

The characterisation of the deodorant composition of the invention presents difficulties, since it cannot be defined solely in terms of substances of specified structure and combinations in specified proportions. Nevertheless, procedures have been discovered that enable the essential materials of the deodorant compositions to be identified by tests.

The essential materials required for the formulation of deodorant compositions are those having a lipoxidase-inhibiting capacity of at least 50% or those having a Raoult variance ratio of at least 1.1, as determined by the following tests, which are designated the lipoxidase and morpholine tests respectively.

THE LIPOXIDASE TEST

In this test the capacity of a material to inhibit the oxidation of linoleic acid by lipoxidase (EC1.12.1.13) to form a hydroperoxide is measured.

Aqueous 0.2 M sodium borate solution (pH 9.0) is used as buffer solution.

A control substrate solution is prepared by dissolving linoleic acid (2.0 ml) in absolute ethanol (60 ml), diluting with distilled water to 100 ml and then adding borate buffer (100 ml) and absolute ethanol (300 ml).

A test substrate solution is prepared in the same way as the control substrate solution except that for the absolute ethanol (300 ml) is substituted the same volume of a 0.5% by weight solution in ethanol of the material to be tested.

A solution of the enzyme lipoxidase in the borate buffer and having an activity within the range of from 15,000 to 40,000 units per ml is prepared.

The activity of the lipoxidase in catalysing the oxidation of linoleic acid is first assayed spectrophotometrically using the control. An automatic continuously recording spectrophotometer is used and the increase in extinction at 234 nm (the peak of hydroperoxide) is measured to follow the course of oxidation, the enzyme concentration used being such that it gives an increase in optical density ($\Delta$OD) at 234 nm within the range of from 0.6 to 1.0 units per minute. The following ingredients are placed in two 3 ml cuvettes.

|  | Control (ml) | Blank (ml) |
| --- | --- | --- |
| Control substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the control cuvette last and the reaction immediately followed spectrophotometrically for about 3 minutes, with recording of the increase in optical density at 234 nm as a curve on a graph.

The capacity of a material to inhibit the oxidation is then measured using a test sample containing enzyme, substrate and a deodorant material. The following ingredients are placed in two 3 ml cuvettes.

|  | Test Sample (ml) | Blank (ml) |
| --- | --- | --- |
| Test sample solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the test sample cuvette last and the course of the reaction immediately followed as before.

The lipoxidase-inhibiting capacity of the material is then calculated from the formula 100 $(S_1-S_2)/S_1$, where $S_1$ is the slope of the curve obtained with the control and $S_2$ is the slope of the curve obtained with the test sample, and thus expressed as % inhibition. A material that gives at least 50% inhibition in the test is hereafter referred to as having a lipoxidase-inhibiting capacity of at least 50%.

The Morpholine Test

In this test the capacity of a material to depress the partial vapour pressure of morpholine more than that required by Raoult's Law is measured. Substances that undergo chemical reaction with morpholine, for example aldehydes, are to be regarded as excluded from the test.

Into a sample bottle of capacity 20 ml is introduced morpholine (lg) the bottle fitted with a serum cap and then maintained at 37° C. for 30 minutes for equilibrium to be reached. The gas in the headspace of the bottle is analysed by piercing the serum cap with a capillary needle through which nitrogen at 37° C. is passed to increase the pressure in the bottle by a standard amount and then allowing the excess pressure to inject a sample from the headspace into gas chromatograph apparatus, which analyses it and provides a chromatographic trace curve with a peak due to morpholine, the area under which is proportional to the amount of morpholine in the sample.

The procedure is repeated under exactly the same conditions using instead of morpholine alone, morpholine (0.25 g) and the material to be tested (lg); and also having the material (lg) without the morpholine to check whether it gives an interference with the morpholine peak (which is unusual).

The procedure is repeated until reproducible results are obtained. The areas under the morpholine peaks are measured and any necessary correction due to interference by the material is made.

A suitable apparatus for carrying out the above procedure is a Perkin-Elmer Automatic GC Multifract F40 for Head Space Analysis. Further details of this method are described by Kolb in "CZ-Chemie-Technik", Vol. 1, No. 2, 87–91 (1972) and by Jentzsch et al in "Z.Anal.-Chem." 236, 96–118 (1968).

The measured areas representing the morpholine concentration are proportional to the partial vapour pressure of the morpholine in the bottle headspace. If A is the area under the morpholine peak when only morpholine is tested and A' is the area due to morpholine when a material is present, the relative lowering of partial vapour pressure of morpholine by the material is given by $1-A'/A$.

According to Raoult's Law, if at a given temperature the partial vapour pressure of morpholine in equilibrium with air above liquid morpholine is p, the partial vapour pressure p' exerted by morpholine in a homogeneous liquid mixture of morpholine and material at the same temperature is $pM/(M+PC)$, where M and PC are the molar concentrations of morpholine and material. Hence, according to Raoult's Law the relative lowering of morpholine partial vapour pressure $(p-p')/p$, is given by $1-M/(M+PC)$, which under the circumstances of the test is $87/(87+m/4)$, where m is the molecular weight of the perfume material.

The extent to which the behaviour of the mixture departs from Raoult's Law is given by the ratio $$\frac{1-A'/A}{87/(87+m/4)}$$

The above ratio, which will be referred to as the Raoult variance ratio, is calculated from the rest results. Where a material is a mixture of compounds, a calculated or experimentally determined average molecular weight is used for m. A material that depresses the partial vapour pressure of morpholine by at least 10% more than that required by Raoult's Law is one in which the Raoult variance ratio is at least 1.1.

A large number of materials which satisfy one or both tests is described later in this specification and these are hereafter referred to a "components", in contrast to other materials which fail both tests which are referred to as "ingredients".

Before defining the more detailed aspects of the invention so far as it relates to deodorant compositions, it is necessary to clarify some of the terms that will be employed.

A composition is a blend of organic compounds. For the purposes of this specification it is necessary to identify the "components" in the composition. This is done by first describing the composition in terms of four categories. These categories are given below. Examples of components in each category are provided.

(1) Single chemical compounds whether natural or synthetic, e.g. coumarin (natural or synthetic), iso-eugenol, benzyl salicylate. The majority of components are in this category.

(2) Synthetic reaction products (products of reaction), mixtures of isomers and possibly homologues, e.g. α-iso-methyl ionone.

(3) Natural oils, gums and resins, and their extracts, e.g. patchouli oil, geranium oil, clove leaf oil, benzoin resinoid.

(4) Synthetic analogues of category 3. This category includes materials that are not strict analogues of natural oils, gums and resins but are materials that result from attempts to copy or improve upon materials of category 3, e.g. Bergamot AB 430, Geranium AB 76, Pomeransol AB 314.

Components of Categories (3) and (4) although often uncharacterised chemically are available commercially.

Where a material is supplied or used conventionally for convenience as a mixture, e.g. p-t-Amylcyclohexanone diluted with diethyl phthalate, for the purposes of this specification two components are present, so that use of 5% of a blend of 1 part of this ketone and 9 parts of diethyl phthalate is represented as 0.5% of the ketone and 4.5% of diethyl phthalate.

It has been found advantageous in formulating the most effective deodorant composition for incorporation into the detergent product of the invention to use components that, as well as satisfying the lipoxidase or morpholine tests, satisfy further conditions. These conditions are:

(i) there must be at least five components present, (ii) each of these components must be selected from at least four different chemical classes (to be defined below), (iii) a component from each of classes 1, 2 and 4 must be present, (iv) at least 45%, preferably at least 50 and most preferably from 60 to 100% by weight of the deodorant composition must comprise components, (v) a component is not considered to contribute to the efficacy of the deodorant composition if it is present in the deodorant composition at a concentration of less than 0.5% by weight, and (vi) a class is not considered to contribute to the efficacy of the deodorant composition if it is present in the deodorant composition at a concentration of less than 0.5% by weight.

Therefore, according to the preferred embodiment of the invention, there is provided a deodorant skin treatment product as herein defined in which the deodorant composition consists essentially of from about 45 to 100% by weight of at least five components and from 0 to about 55% by weight of ingredients, each of the components being selected from components having a lipoxidase inhibiting capacity of at least 50% and components having a Raoult variance ratio of at least 1.1, the components and ingredients being so chosen that the deodorant value of the deodorant composition is within the range 0.50 to 3.5.

Each component should be allocated to one of six classes; These classes are:

Class 1—Phenolic substances;
Class 2—Essential oils, extracts, resins, "synthetic" oils (denoted by "AB");
Class 3—Aldehydes and ketones;
Class 4—Polycyclic compounds;
Class 5—Esters;
Class 6—Alcohols.

In attributing a component to a class, the following rules are to be observed. Where the component could be assigned to more than one class, the component is allocated to the class occurring first in the order given above: for example clove oil, which is phenolic in character, is placed in Class 1 although it otherwise might have been allocated to Class 2. Similarly, 2-n-heptyl cyclopentanone which is a polycyclic ketone is attributed to Class 3 instead of Class 4.

The following are examples of deodorant components that either have a lipoxidase inhibiting capacity (LIC) of at least 50% or have a Raoult variance ratio (RVR) of at least 1.1. Their class, molecular weight (m), LIC and RVR as determined by the tests already described herein are also listed.

The nomenclature adopted for the components listed below and for the ingredients which appear in the deodorant formulations of the Examples is, so far as is possible, that employed by Steffen Arctander in "Perfume and Flavour Chemicals (Aroma Chemicals)" Volume I and II (1969) and the "Perfume & Flavour Materials of Natural Origin" (1960) by the same author. Where a component or other ingredient is not described by Arctander, then either the chemical name is given or, where this is not known (such as is the case with perfumery house specialities), then the supplier's identify can be established by reference to the appendix which appears at the end of the specification.

|  | LIC | RVR | m |
|---|---|---|---|
| Class 1 - Phenolic Substances | | | |
| iso-Amyl salicylate | 95 | 1.24 | 208 |
| Benzyl salicylate | 0 | 1.58 | 228 |
| Carvacrol | 32 | 1.43 | 150 |
| Clove leaf oil | 79 | 1.43 | 164 |
| Ethyl vanillin | 100 | 1.43 | 152 |
| iso-Eugenol | 100 | 1.48 | 164 |
| LRG 201 | 100 | 1.21 | 196 |
| Mousse de chene Yugo | 98 | 1.29 | 182 |
| Pimento leaf oil | 100 | — | 165 |
| Thyme oil red | 55 | 1.37 | 150 |
| Class 2 - Essential oils, extracts, resins, "synthetic" oils, (denoted by "AB") | | | |
| Benzoin Siam resinoids | 87 | — | — |
| Bergamot AB 37 | 58 | 0.97 | 175 |
| Bergamot AB 430 | 58 | 0.97 | 175 |
| Geranium AB 76 | 26 | 1.29 | 154 |
| Geranium oil | 26 | 1.29 | 154 |
| Opoponax resinoid | 96 | 1.33 | 150 |
| Patchouli oil | 76 | 1.25 | 140 |
| Petitgrain oil | 34 | 1.27 | 175 |
| Pomeransol AB 314 | 100 | — | — |
| Class 3 - Aldehydes and Ketones | | | |
| 6-Acetyl-1,1,3,4,4,6-hexamethyl-tetrahydronaphthalene | 100 | 1.03 | 258 |
| p-t-Amyl cyclohexanone | 50 | 1.10 | 182 |
| p-t-Butyl-α-methyl hydrocinnamic aldehyde | 74 | — | 204 |
| 2-n-Heptylcyclopentanone | 56 | 1.05 | 182 |
| α-iso-Methyl ionone | 100 | 1.13 | 206 |
| β-Methyl naphthyl ketone | 100 | 0.96 | 170 |
| Class 4 - Polycyclic Compounds | | | |
| Coumarin | 58 | 1.22 | 146 |
| 1,3,4,6,7,8-Hexahydro-4,6,6,7,8,8-hexamethyl cyclopenta-α-2-benzopyran | 100 | — | 240 |
| 3a-Methyl-dodecahydro-6,6,9a-trimethylnaphtho(2,1-b)furan | 58 | 1.30 | 230 |
| β-Naphthyl methyl ether | 100 | — | 158 |
| Class 5 - Esters | | | |
| o-t-Butylcyclohexyl acetate | 52 | 1.08 | 198 |

-continued

|  | LIC | RVR | m |
|---|---|---|---|
| p-t-Butylcyclohexyl acetate | 54 | 0.98 | 198 |
| Diethyl phthalate | 79 | 1.20 | 222 |
| Nonanediol-1,3-diacetate | 33 | 1.17 | 244 |
| Nonanolide-1:4 | 92 | 0.87 | 156 |
| i-Nonyl acetate | 50 | 0.83 | 186 |
| i-Nonyl formate | 19 | 1.49 | 172 |
| Class 6 - Alcohols | | | |
| Dimyrcetol | 16 | 1.22 | 156 |
| Phenylethyl alcohol | 22 | 1.24 | 122 |
| Tetrahydromuguol | 24 | 1.23 | 158 |

It has been shown that for best results, a certain minimum average concentration of components should be present. This minimum concentration is a function of the number of classes present—the more classes present, the lower the minimum concentration. The minimum average concentration in the various situations that can apply is shown in the Table below:

| Number of classes represented in deodorant composition | Average concentration of components | |
|---|---|---|
| | minimum not less than (%) | preferably not less than (%) |
| 4 | 5 | 6 |
| 5 | 4.5 | 5.5 |
| 6 | 4.5 | 5 |

Also, it is preferred that at least 1% of each of four classes is present in the deodorant composition, but individual components which are present at a concentration of less than 0.5% are eliminated from this calculation, as is the class into which they fall if there is present no component at a concentration of at least 0.5% which falls within that class.

More specifically, the invention also provides a deodorant skin treatment product as herein defined wherein the amount of deodorant components in the deodorant composition present in the classes 1,2 and 4 as herein defined is at least 1%, more preferably at least 3% by weight of the deodorant composition for each class, and the amount of components present in each of at least two other classes is at least 1% by weight of the composition, provided also that any component that is present in the deodorant composition at a concentration of less than a threshold value of 0.5% by weight is eliminated from the calculation of the amounts of components in each class.

Although at least four different classes of components should preferably be represented in the deodorant composition, superior compositions can be obtained if more than four classes are represented. Accordingly, five or six classes can be represented in the deodorant composition.

It has been shown by the preparation, examination and testing of many hundreds of deodorant compositions that the best results are obtained by keeping within the aforementioned rules when selecting types and amounts of components and ingredients. For example, deodorant compositions which contain less than the minimum concentration of components of 45% are unlikely to result in a deodorant composition having a deodorant value of at least 0.50. Therefore, in preparing the best deodorant compositions of the invention, the rules for selection of components according to their classification, the representation of different classes, the amounts of each component present, bearing in mind the threshold value below which it is believed a component will not significantly contribute, are all important to observe if the best results are to be obtained.

It should be explained that components present in the deodorant skin treatment product for purposes other than obtaining deodorant effects, for example an adjunct like the anti-oxidant, are excluded from the operation of the preceding instructions to the extent that the component is required for that other purpose. The levels at which adjuncts are conventionally present in skin treatment products is well-established for established materials Zand readily determinable for new materials so that the application of the above exclusion presents no difficulty.

Deodorant compositions can be incorporated in deodorant skin treatment products according to the invention at a concentration of from about 0.01 to about 20%, preferably from 0.5 to 10% and most preferably from 1 to 5% by weight.

It is apparent that if less than 0.01% of a deodorant composition is employed, then use of the skin treatment product is unlikely to provide a significant reduction in body malodour intensity. If more than 20% of a deodorant composition is employed, then use of the skin treatment product is unlikely to further reduce body malodour intensity beyond that observed at the 20% level.

THE VEHICLE

Following the discovery that when a deodorant composition is applied to human skin it was capable of effecting a reduction in body malodour over a prolonged period, it was apparent that many different types of products for application to the skin or hair could be formulated. It was, however, necessary to include a cosmetically acceptable vehicle with the deodorant composition, as it was otherwise not possible, under normal conditions of use by the consumer, to effectively distribute an appropriate amount of the deodorant composition onto the skin or the hair. Suitable vehicles can be classified as described hereinafter.

It should be explained that vehicles are materials which can act as diluents, dispersants or carriers for the deodorant composition and which therefore ensure that it can be applied to and distributed evenly over the skin or the hair at an appropriate concentration. It is not intended that soap or non-soap detergents, which could also act as vehicles, are to be excluded; they can certainly be present in many of the products according to the invention, but it is intended that these products should also contain at least one vehicle other than soap or non-soap detergents.

The vehicles that can be used in products according to the invention can include powdered absorbents, binders and carriers, and liquid such as emollients, propellants, solvents, humectants and thickeners. Examples of each of these types of vehicles are as follows:

POWDERED ABSORBENTS

Magnesium silicate
Amorphous silica powder
Cross-linked starch
Anionic polyelectrolytes other than cross-linked starch
Base hydrolysed starch/polyacrylonitrile graft copolymer An example of cross-linked starch is a substantially water-insoluble cross-linked gelatinised starch, in which the degree of substitution of the cross-linking groups is 0.001 to 0.04, which is preferably, but not necessarily, substituted by ionic groups attached to the starch by ether linkages, these groups, when present, being associated with mono- or di-valent counterions.

Although the degree of substitution of the cross-linking groups can be relatively low, the cross-linked starch is substantially insoluble in water.

The cross-linking of the starch molecules may be effected by ether bridges of the formula —O—R—O, where R is an aliphatic group, which may be substituted by one or more hydroxy groups, consisting 1 to 10 carbon atoms. Preferably R is $CH_2CH(OH)CH_2$—, which is the case when the starch is cross-linked using epichlorhydrin as cross-linking agent.

The ionic groups, when present, preferably have the formula $Z—R^1$ and $R^1$ is an alkylene group selected from carbon atoms and Z is an anionic group selected from carboxyl, sulphonic or phosphonic groups or a cationic group of the formula:

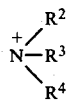

where $R^2$ is hydrogen or lower alkyl, and $R^3$ and $R^4$ are lower alkyl or are alkylene groups linked together to form a five or six-membered heterocyclic ring. Particularly suitable materials are those where $R^1$ is an alkylene group containing 1 or 2 carbon atoms and Z is —COO$^-$ and preferred materials are carboxymethylated cross-linked gelatinised starches.

When Z is an anionic group, the counterion preferably is an alkali metal, alkaline earth metal, ammonium or substituted ammonion ion. The substituted ammonium derivatives may be those in which one or mre hydrogen atoms are replaced by $C_{1-4}$ alkyl or $C_{2-4}$ hydroxyalkyl groups or in which the nitrogen atom forms part of a heterocyclic ring. An example of such a substituted ammonium ion is tetramethylammonium. Preferred counterions when Z is an anionic group are the sodium, potassium and ammonium ions. When Z is a cationic group, the counterion may be, for example, chloride, bromide or sulphate.

Particularly preferred powdered absorbents are the sodium and ammonium salts of carboxymethylated epichlorhydrin cross-linked gelatinised starch having a water absorption value of at least 5 and being insoluble in water to the extent of at least 99% by weight.

Cross-linked gelatinised starch can be prepared by the process described in our British Patent Application No 2118/77.

Examples of the anionic polyelectrolyte, other than the cross-linked starches as hereinbefore defined, are water-insoluble ionic complexes of a water-soluble anionic polyelectrolyte and a polyvalent metal cation having a valency of at least three, the cation being present in the amount of 0.01 to 5.0 milliequivalents per gram of polyelectrolyte.

The polyelectrolyte generally contains anionic groups, such as carboxylate, sulphonate, sulphate and phosphate groups or mixtures thereof. Preferably the polyelectrolyte is polyacrylic acid.

The cation is a transition metal, preferably aluminium, iron, chromium, zirconium, titanium or mixtures thereof. The cation is preferably present in the amount of 0.1 to 1.0 milliequivalents per gram of polyelectrolyte.

A particularly preferred polyelectrolyte is polyacrylic acid having from 40 to 85% of its carboxylate groups neutralised, the cation being aluminium which is present in the amount of from 0.1 to 1.0 milliequivalents per gram of polyelectrolyte.

These polyelectrolytes and their preparation are further described in German Patent Application (DTOLS) No. 2 609 114 (National Starch and Chemical Corporation).

Further examples of the anionic polyelectrolyte are water-insoluble covalently cross-linked anionic polyelectrolytes.

The anionic polyelectrolytes can be water-soluble polyelectrolytes which are covalently cross-linked to render them insoluble yet incapable of absorbing water.

Examples of these water-soluble anionic polyelectrolytes to be covalently cross-linked are natural polymers, such as anionic derivatives of starch and cellulose, and synthetic polymers such as carboxylic homopolymers and copolymers containing at least 20 mole percent carboxylic acid units as polyacrylic acid.

Examples of the covalent cross-linking compounds which can be copolymerised with the polyelectrolytes are divinyl compounds, such as divinyl benzene, divinyl diethylene glycol diether, divinyl diphenyl silicone and divinyl sulphone; allyl compounds, such as triallyl cyanurate, trimethylol propane diallyl ether, allyl methacrylate, allyl acrylate, allyl crotonate, diallylphthalate, diallyl succinate and diallyl sucrose; polyfunctional acrylates and methacrylates, such as tetraethylene glycol diacrylate, triethylene glycol dimethacrylate, pentaerythritol tetra acrylate, ethylidene dimethylacrylate and trimethylol propane trimethyacrylate; and polyfunctional arylamide and methacrylamides, such as N,N'-methylene bis-acrylamide and N,N'-methylene bis-methacrylamide.

These water-insoluble covalently cross-linked anionic polyelectrolytes and their preparation are further described in Netherlands Patent Application No 7 604 518 (National Starch and Chemical Corporation).

Any of the water-insoluble anionic polyelectrolyte complexes as herein described can be surface treated with a polyvalent metal cation to maximise absorption by the polymer particles of moisture.

The preferred polyvalent metal cations for surface treatment are aluminum, zirconium, chromium, titanium and zinc.

These surface-treated water-insoluble anionic polyelectrolyte complexes and their preparation are also further described in Netherlands Patent Application No 7 604 518 (National Starch and Chemical Corporation).

An example of a surface treated anionic polyelectrolyte is National Starch Resyn 78-3803 which is potassium polyacrylate cross-linked with aluminium.

Examples of the base hydrolysed starch polyacrylonitrile graft copolymer are those comprising water-insoluble alkali metal salts of saponified gelatinised starch and saponified polyacrylonitrile in mole ratios of from 1:1.5 to 1:9. Copolymers such as these are identified and prepared by the methods set out in Journal of Applied Polymer Science, Volume 13, pages 2007–2017 (1969), and Volume 15, pages 3015–3024 (1971).

Further examples of vehicles are classified as follows:

Powdered binders and carriers

Microcrystalline cellulose
Isostearyl neopentanoate
Polyacrylamide

Lauryl lactate
Precipitated silica
Talc
Chalk

Emollients

Stearyl alcohol
Glyceryl monoricinoleate
Glyceryl monostearate
Sulphated tallow
Propylene glycol
Mink oil
Cetyl alcohol
Stearyl stearate
Isopropyl isostearate
Dimethyl brassylate
Stearic acid
Isobutyl palmitate
Isocetyl stearate
Oleyl alcohol
Isopropyl laurate
Hexyl laurate
Decyl oleate
Di-isopropyl adipate
2-octadodecanol
Iso-cetyl alcohol
Myristyl ethoxymyristate
Cetyl palmitate
Dimethylpolysiloxane
Di-isopropyl adipate
Di-n-butyl sebacate
Di-isopropyl sebacate
Di-2-ethyl hexyl sebacate
2-ethyl hexyl palmitate
Isononyl isononanoate
Isodecyl isononanoate
Isotridecyl isononanoate
2-ethyl hexyl palmitate
2-ethyl hexyl stearate
Di-(2-ethyl hexyl) adipate
Di-(2-ethyl hexyl) succinate
Isopropyl myristate
Isopropyl palmitate
Isopropyl stearate
Butyl stearate
Glyceryl monostearate
Polyethylene glycols
Propylene glycol
Triethylene glycol
Lanolin
Castor oil
Acetylated lanolin alcohols
Acetylated lanolin
petrolatum
Isopropyl ester of lanolin fatty acids
Mineral oils
Butyl myristate
Isostearic acid
Palmitic acid
Isopropyl linoleate
Cetyl lactate
Lauryl lactate
Myristyl lactate
Quaternised hydroxy alkyl aminogluconate
Decyl oleate
Isodecyl oleate
Di-isopropyl adipate
2-ethyl hexyl palmitate
Isostearyl neo pentanoate
Myristyl myristate
Di-isopropyl adipate
Oleyl ethoxy myristate
Diglycol stearate
Ethylene glycol monostearate
Myristyl stearate
Isopropyl lanolate

Propellants

Trichlorofluoro methane
Dichloro difluoro methane
Dichloro tetrafluoro ethane
Monochloro difluoro methane
Trichloro trifluoro ethane
Propane
Butane
Isobutane
(used singly or in admixture)

Solvents

Ethyl alcohol
2-ethylhexanol
Ethylene carbonate
Propylene carbonate
N-methyl glucamine
Castor oil
Linear ethoxylated polymer of methanol
Ethylene glycol monoethyl ether
Diethylene glycol monobutyl ether
Diethylene glycol monoethyl ether
Propoxylated butanol
Propoxylated oleyl alcohol
Butyl stearate
Butyl myristate

Humectants

Glycerin
Sorbitol
Sodium 2-pyrrolidone-5-carboxylate
Soluble collagen
Dibutyl phthalate
Gelatin
Polyglycerogen
Ethoxylated (10–20 moles) glucose
Propoxylated (10–20 moles) glucose

Thickeners

Gums
Starch
Coloidal silicon dioxide
Sodium polyacrylate
Tetra alkyl and/or trialkyl aryl ammonium smectites
Chemically modified magnesium aluminium silicate
Organically modified montmorillonite clay
Hydrated aluminium silicate
Fumed silica
Carboxyvinyl polymer
Sodium carboxymethyl cellulose
Hydroxyethyl stearate amide
Ethylene glycol monostearate The quantity of vehicle employed can constitute the balance of the product, i.e. up to 99.99% by weight, especially from 80 to 99.99% by weight when the product consists solely of deodorant composition and vehicle, less than 80% by weight of vehicle can be present when other ingredients as hereinafter defined are present, provided that the vehicle is capable of functioning in the manner defined herein.

Other Ingredients

The products according to the invention can contain ingredients other than those already mentioned, depending on the form of the intended product. It is, for example, possible to include moisturisers, antiseptics or preservatives, anti-oxidants, anti-caking agents, emulsifiers, perfumes and colouring agents. Examples of some of the ingredients are as follows:

Moisturisers

Sodium pyrrolidone carboxylate
Sodium lactate
Orotic acid

Antiseptics and preservatives

Cetyl pyridinium chloride
Tribromosalicylanilide
Trichlorocarbanilide
Benzalkonium chloride
Trichlorohydroxydiphenyl ether

Antioxidants

Ascorbyl palmitate
Propyl gallate
Butylated hydroxy toluene
Butylated hydroxyanisole

Anti-caking agents

Hydrophobic starch
Sulphonated formaldehyde
Silicone dioxide

Anionic emulsifiers

Potassium stearate
Sodium stearate
Ammonium stearate
Triethanolamine stearate
Glyceryl monostearate containing either potassium or sodium soap
Sodium lauryl sulphate
Sodium cetyl sulphate
Glyceryl monostearate containing sodium lauryl sulphate

Cationic emulsifiers

N(stearoyl)colamino formylmethyl pyridinium chloride
N-soya-N-ethyl morpholinium ethosulphate
Alkyl dimethyl benzyl ammonium chloride
Di-isobutylphenoxyethoxy ethyl dimethyl benzyl ammonium chloride
Cetyl pyridinium chloride; and

Nonionic emulsifiers

Fatty acid esters of sorbitan anhydrides of ethylene oxide products of sorbitan fatty acid esters such as Span 80 or Tween 80; and pluronics which are addition products of hydrophilic polyoxyethylene groups and a hydrophilic polyoxypropylene.

The amount of emulsifiers, if used, usually forms from 1 to 10%, preferably 1 to 5% by weight of the product.

Process for Preparing Deodorant Skin Treatment Products

The process for preparing deodorant skin treatment products thereby employing a deodorant composition as a means for inhibiting body malodour development comprises mixing from 0.01 to 20% by weight of a deodorant composition with up to 99.99% by weight of a cosmetically acceptable vehicle for the composition to provide a deodorant skin treatment product, the deodorant composition preferably having a deodorant value of at least 0.50 as measured by the Deodorant Value Test. The selection of a suitable vehicle for the deodorant composition and a suitable amount to be employed in the process of the invention will depend upon the nature of the required skin treatment product, for example, whether it is solid or liquid.

Usually it is convenient to add the deodorant composition to the vehicle at a stage towards the end of its manufacture so that loss of any volatile ingredients such as may occur during a heating step is minimised.

It is furthermore usual to incorporate the deodorant composition in such a manner that it is thoroughly mixed with the other ingredients and is uniformly distributed throughout the skin treatment product.

Method of Using the Deodorant Skin Treatment Product

The deodorant skin treatment product of the invention is to be employed particularly for suppressing human body malodour, by applying it topically, directly to the skin or hair. The deodorant skin treatment product is particularly effective when applied to the regions of the human skin where apocrine sweat glands are most abundant, notably in the groin, axilla, anal and genital regions and in the aureola of the nipple.

Products of the Invention

The deodorant skin treatment product of the invention can take many forms, depending upon whether it is intended for application to the skin or the hair in the form of a powder, lotion, cream or liquid spray.

Examples of products of the invention can be classified according to their mode of use, but it is to be understood that the invention is not limited solely to these Examples.

Examples of products of the invention which are personal products intended for application to the skin or hair include talcum powder, deodorant foot powder, solid bath products such as bath cubes and bath salts, sunscreen oil, body lotion, body perfume, bath oils, depilatories, skin deodorants, including aerosols and creams or lotions, including those intended for application as a stick or from a roll-ball applicator.

Examples of the Invention

The invention is illustrated by the following Examples which exemplify deodorant skin treatment products.

It should be noted that each of these products was evaluated in a manner similar to that described for the Deodorant Value Test referred to hereinbefore. However, in view of the fact that testing the products involved the assessment of body malodour following application to the axillae of a product other than a soap bar (instead of by washing the axillae with a standard soap bar containing the deodorant composition previously described as the Deodorant Value Test) the effectiveness of each product was expressed in terms of "odour reduction value".

It should be recognised that if an odour reduction value of less than 0.50 is recorded following use of products of the invention, it is indicative that insufficient deodorant composition has been transferred to the skin of the axilla, rather than evidence that the product itself contains insufficient of a deodorant composition as herein defined.

Example 1

A deodorant talcum powder was prepared by mixing together talc and a deodorant composition in the following proportions:

|  | % by weight |
|---|---|
| Talc | 99.5 |
| Deodorant Composition I | 0.5 |

A control consisting solely of talc was also provided for comparison.

The deodorant composition employed in this Example had the following formulation:

| Deodorant Composition 1 | | | |
|---|---|---|---|
|  | Parts | Class | Total in class |
| Components |  |  |  |
| iso-Amyl salicylate | 5.0 | 1 |  |
| Benzyl salicylate | 4.0 | 1 | 10.25 |
| LRG 201 | 1.25 | 1 |  |
| Bergamot AB 430 | 15.0 | 2 |  |
| Geranium AB 76 | 4.0 | 2 | 20.7 |
| Opoponax resinoid | 1.7 | 2 |  |
| 1,3,4,6,7,8-Hexahydro-4,6,6,7,8,8-hexamethyl-cyclopenta-α-2-benzopyran | 10.0 | 4 | 10.0 |
| o-t-Butylcyclohexyl acetate | 0.5 | 5 |  |
|  |  |  | 4.25 |
| Diethyl phthalate | 3.75 | 5 |  |
| Nonanolide-1.4 | 0.2* | (5) |  |
| Ingredients |  |  |  |
| Amber AB 358 | 3.0 |  |  |
| Benzyl alcohol | 0.15 |  |  |
| Cedar atlas oil | 5.0 |  |  |
| Citronellol | 7.0 |  |  |
| Citronella oil | 16.1 |  |  |
| Citronellyloxyacetaldehyde | 0.5 |  |  |
| Hexyl aldone | 0.7 |  |  |
| Jasmin AB 284 | 12.0 |  |  |
| Orange oil sweet | 8.0 |  |  |
| 10-Undecen-1-al | 0.15 |  |  |
| Vetyvert oil | 2.0 |  |  |
|  | 100.0 |  |  |

*eliminated from calculation - below threshold value of 0.5%.

| Total amount of components | 45.2 |
|---|---|
| Number of components present | 9 |
| Average amount of each component | 5.0 |
| Number of classes represented | 4 |

In this Example, the deodorant effectiveness of a talcum powder according to the invention was evaluated in terms of its odour reduction value in the following manner:

A standard quantity of 0.1 g of either the test or the control talcum powder product was applied to the axillae of the panel of human subjects. The axilliary odour was then judged by trained assessors and the odour scores using the 0 to 5 scale were recorded and subjected to statistical analysis to obtain average scores.

| Results of Odour Reduction Value Test 1 using Talcum Powder | | |
|---|---|---|
|  | Control powder | Test powder |
| Average scores | 2.36 | 2.01 |
| Odour reduction value |  | 0.35 |

EXAMPLE 2

A general purpose deodorant water-in-oil skin cream was prepared by homogenising the following ingredients in the proportions stated:

|  | % by weight |
|---|---|
| Phase A |  |
| Liquid lanolin absorption base (Liquid Base C 3929) | 12 |
| Lanolin alcohol (Hartolite) | 3.16 |
| Ozokerite wax | 2.5 |
| Microcrystalline petroleum wax (Cosmolloid wax) | 4.6 |
| Light mineral oil (Puremor 210) | 10.14 |
| Cetyl alcohol | 0.3 |
| Phase B |  |
| Glycerol | 2.5 |
| Magnesium sulphate | 0.7 |
| Deoionised water | to 100 |
| Phase C |  |
| Deodorant Composition 2 | 0.5 |

The cream was prepared by heating Phase A and Phase B separately to a temperature of 75° C. and then adding Phase B to Phase A with rapid stirring. The mixture was stirred well until cool and finally Phase C was added with stirring.

A control cream from which the deodorant composition had been omitted was also provided for comparison.

The deodorant composition employed in this Example had the following formulation:

| Deodorant Composition 2 | | | |
|---|---|---|---|
|  | Parts | Class | Total in class |
| Components |  |  |  |
| Carvacrol | 3.5 | 1 |  |
|  |  |  | 4.5 |
| Thyme oil red | 1.0 | 1 |  |
| Bergamot AB 37 | 20.0 | 2 |  |
| Pomeransol AB 413 | 6.0 | 2 | 30.0 |
| Petitgrain oil | 4.0 | 2 |  |
| 6-Acetyl-1,1,3,4,4,6-hexamethyl-tetrahydro-naphthalene | 3.0 | 3 | 8.0 |
| β-Methyl naphthyl ketone | 5.0 | 3 |  |
| 3a-Methyl-dodecahydro-6,6,-9a-trimethyl naphtho-(2,1-b)furan | 0.25* | (4) |  |
| β-Naphthol methyl ether | 9.0 | 4 | 9.0 |
| Ingredients |  |  |  |
| Citronellyl acetate | 5.0 |  |  |
| Dipropylene glycol | 4.75 |  |  |
| Geranyl nitrile | 1.5 |  |  |
| Indole | 1.0 |  |  |
| Lemongrass oil | 3.0 |  |  |
| Lime AB 402 | 10.0 |  |  |
| Lavendin oil | 4.0 |  |  |
| l-Menthol | 8.0 |  |  |
| Neroli AB 78 | 6.0 |  |  |
| Orange oil sweet | 5.0 |  |  |
|  | 100.0 |  |  |

*eliminated for calculation - below threshold value of 0.5%

Total amount of components—51.5
Number of components present—8
Average amount of each component—6.4
Number of classes represented—4

In this Example, the deodorant effectiveness of a skin cream according to the invention was evaluated in terms of its odour reduction value in the following manner.

A standard quantity of 0.25 g of either the test or the control skin cream product was applied to the axillae of the panel of human subjects. The axilliary odour was then judged by trained assessors and the odour scores using the 0 to 5 scale were recorded and subjected to statistical analysis to obtain average scores.

| Results of Odour Reduction Value Test 2 using Skin Cream | | |
|---|---|---|
| | Control cream | Test cream |
| Average scores | 2.31 | 0.33 |
| Odour reduction value | | 1.98 |

EXAMPLE 3

A deodorant oil-in-water hand lotion was prepared by homogenising the following ingredients in the proportions stated:

| | % by weight |
|---|---|
| Phase 1 | |
| Stearic acid (triple pressed) | 1 |
| Puremor 210 | 3 |
| Cetyl alcohol | 0.3 |
| Glycerol monostearate | 0.6 |
| Phase 2 | |
| Triethanolamine | 0.3 |
| Glycerol | 2.0 |
| Preservative | q.s. |
| Deionised water | to 100 |
| Phase 3 | |
| Deodorant Composition 3 | 0.5 |
| Colour | 0.5 |

Phases 1 and 2 were heated separately to 70° C. and then Phase 2 was added to Phase 1 with stirring. Phase 3 was finally added with stirring when the temperature of the mixture had fallen to 40° C.

A control lotion from which the deodorant composition had been omitted was also provided for comparison.

The deodorant composition employed in this Example had the following formulation:

| Deodorant Composition 3 | | | |
|---|---|---|---|
| | Parts | Class | Total in class |
| Components | | | |
| Mousse de chene Yugo | 1.25 | 1 | |
| Pimento leaf oil | 10.0 | 1 | 11.25 |
| Benzoin Siam resinoids | 5.0 | 2 | |
| Bergamot AB 430 | 15.0 | 2 | 25.0 |
| Geranium oil | 5.0 | 2 | |
| p-t-Amylcyclohexanone | 5.0 | 3 | |
| α-iso-Methyl ionone | 12.0 | 3 | 17.0 |
| Coumarin | 4.0 | 4 | |
| 1,3,4,6,7,8-Hexahydro-4,6,6,7,8,8-hexamethyl-cyclopenta-α-2-benzopyran | 3.0 | 4 | 7.0 |
| Diethyl phthalate | 4.35 | 5 | 4.35 |
| Ingredients | | | |
| Hercolyn D | 12.25 | | |
| Lavandin oil | 10.0 | | |
| Musk ambrette | 3.0 | | |
| Rosenta AB 380 | 10.0 | | |
| Rose-D-oxide | 0.15 | | |
| | 100.0 | | |

Total amount of components—64.6
Number of components present—10
Average amount of each component—6.5
Number of classes represented—5

In this Example, the deodorant effectiveness of a hand lotion according to the invention was evaluated in terms of its odour reduction value in the following manner:

A standard quantity of 0.25 g of either the test or the control hand lotion product was applied to the axillae of the panel of human subjects. The axilliary odour was then judged by trained assessors and the odour scores using the 0 to 5 scale were recorded and subjected to statistical analysis to obtain average scores.

| Results of Odour Reduction Value Test 3 using Hand Lotion | | |
|---|---|---|
| | Control lotion | Test lotion |
| Average scores | 2.70 | 1.59 |
| Odour reduction value | | 1.11 |

EXAMPLE 4

A deodorant body oil for pump pack application was prepared by blending together the following ingredients in the proportions stated:

| | % by weight |
|---|---|
| 2-octyl-dodecanol (Eutanol G) | 30 |
| iso-Propyl myristate | 20 |
| Mineral oil | to 100 |
| Deodorant composition | 1 |

A control oil from which the deodorant composition had been omitted was also provided for comparison.

The deodorant composition employed in this Example had the following formulation:

| Deodorant Composition 4 | | | |
|---|---|---|---|
| | Parts | Class | Total in class |
| Components | | | |
| Ethyl vanillin | 0.2* | (1) | |
| iso-Eugenol | 5.0 | 1 | |
| LRG 201 | 1.25 | 1 | 6.25 |
| Bergamot AB 430 | 8.0 | 2 | |
| Patchouli oil | 7.0 | 2 | 15.0 |
| 2-n-Heptylcyclopentanone | 0.5 | 3 | |
| α-iso-Methyl ionone | 5.0 | 3 | 5.5 |
| β-Naphthol methylether | 7.5 | 4 | 7.5 |
| p-t-Butylcyclohexyl acetate | 4.3 | 5 | |
| Diethyl phthalate | 8.25 | 5 | |
| i-Nonyl formate | 5.0 | 5 | 26.55 |
| Nonanediol-1,3-diacetate | 4.0 | 5 | |
| Phenylethyl phenyl acetate | 5.0 | 5 | |
| Tetrahydro muguol | 6.0 | 6 | 6.0 |
| Ingredients | | | |

Deodorant Composition 4 -continued

| | Parts | Class | Total in class |
|---|---|---|---|
| Citronella oil | 6.0 | | |
| Green Herbal AB 502 | 15.0 | | |
| Indole | 1.5 | | |
| Rosenta AB 380 | 6.0 | | |
| Sandalone | 4.0 | | |
| α-Undecalactone | 0.5 | | |
| | 100.0 | | |

*eliminated from calculation - below threshold value of 0.5%

Total amount of components—66.8
Number of components present—14
Average amount of each component—4.8
Number of classes represented—6

In this Example, the deodorant effectiveness of a body oil according to the invention was evaluated in terms of its odour reduction value in the following manner:

A standard quantity of 0.25 g of either the test or the control body oil product was sprayed onto the axillae of the panel of human subjects. The axilliary odour was then judged by trained assessors and the odour scores using the 0 to 5 scale were recorded and subjected to statistical analysis to obtain average scores.

Results of Odour Reduction Value Test 4 using Body Oil

| | Control oil | Test oil |
|---|---|---|
| Average scores | 2.28 | 0.08 |
| Odour reduction value | | 2.20 |

EXAMPLE 5

A deodorant 'eau de cologne' toilet water was prepared by blending together the following ingredients in the proportions stated:

| | % by weight |
|---|---|
| Ethanol | 80 |
| Deionised water | to 100 |
| Deodorant Composition 5 | 2 |

The blend was allowed to mature for 10 days, refrigerated for 2 further days and finally filtered before use.

A control 'toilet water' from which the deodorant composition had been omitted was also provided for comparison.

The deodorant composition employed in this Example had the following formulation:

Deodorant Composition 5

| | Parts | Class | Total in class |
|---|---|---|---|
| Components | | | |
| Benzyl salicylate | 15.0 | 1 | 21.0 |
| Mousse de chene Yugo | 6.0 | 1 | |
| Bergamot AB 430 | 15.0 | 2 | 15.0 |
| 6-Acetyl-1,3,3,4,4,6-hexamethyl tetrahydronaphthalene | 2.5 | 3 | 2.5 |
| p-t-Amylcyclohexanone | 0.06* | (3) | |
| 3a-Methyl-dodecahydro-6,6,9a-trimethyl-naphtho-2(2,1-b)furan | 0.75 | 4 | 0.75 |
| Diethyl phthalate | 8.04 | 5 | 8.04 |
| Nonanolide-1,4 | 0.2* | (5) | |
| Dimyrcetol | 16.0 | 6 | 16.0 |

Deodorant Composition 5 -continued

| | Parts | Class | Total in class |
|---|---|---|---|
| Ingredients | | | |
| Cinnamic alcohol | 5.0 | | |
| Dimethyl benzyl carbinyl acetate | 2.5 | | |
| Dipropylene glycol | 14.25 | | |
| Geraniol | 5.0 | | |
| iso-Butyl phenyl acetate | 5.0 | | |
| Methyl salicylate | 0.5 | | |
| Pelargene | 4.0 | | |
| Trichloromethyl phenyl carbinyl acetate | 0.2 | | |
| | 100.0 | | |

*eliminated from calculation - below threshold value for a component of 0.5%

Total amount of components—63.29
Number of components present—7
Average amount of each component—9.0
Number of classes represented—6

In this Example, the deodorant effectiveness of a toilet water according to the invention was evaluated in terms of its odour reduction value in the following manner:

A standard quantity of 0.25 g of either the test or the control toilet water product was applied to the axillae of the panel of human subjects. The axilliary odour was then judged by trained assessors and the odour scores using the 0 to 5 scale were recorded and subjected to statistical analysis to obtain average scores.

Results of Odour Reduction Value Test 5 using Toilet Water

| | Control liquid | Test liquid |
|---|---|---|
| Average scores | 1.93 | 0.07 |
| Odour reduction value | | 1.86 |

EXAMPLE 6

A deodorant roll-on lotion was prepared from the following ingredients in the proportions stated:

| | % by weight |
|---|---|
| Industrial Methylated Spirit | 40 |
| Hydroxyethyl cellulose (Natrosol H 250 1% solution) | 40 |
| Deionised water | to 100 |
| Deodorant Composition 6 | 0.5 |

The water was heated to 70°–75° C. and the Natrosol was added with vigorous stirring and the mixture allowed to cool. Alcohol and the deodorant composition were finally added with stirring.

A control roll-on lotion from which the deodorant composition had been omitted was also provided for comparison.

The deodorant composition employed in this Example had the following formulation:

Deodorant Composition 6

| | Parts | Class | Total in class |
|---|---|---|---|
| Components | | | |
| Clove leaf oil | 10.0 | 1 | 11.25 |
| LRG 201 | 1.25 | 1 | |
| Petitgrain oil | 10.0 | 2 | 10.0 |
| p-t-Butyl- -methyl hydro | | | |

-continued

| Deodorant Composition 6 | Parts | Class | Total in class |
|---|---|---|---|
| cinnamic aldehyde | 15.0 | 3 | 15.0 |
| 3a-Methyl-dodecahydro-6,6-9a-trimethylnaphtho-2-(2,1-b)furan | 0.5 | 4 | 0.5 |
| o-t-Butylcyclohexyl acetate | 2.0 | 5 | |
| Diethyl phthalate | 9.25 | 5 | 21.25 |
| i-Nonyl acetate | 10.0 | 5 | |
| Phenyl ethyl alcohol | 10.0 | 6 | 10.0 |
| Ingredients | | | |
| Benzyl propionate | 4.0 | | |
| Bergamot oil | 15.0 | | |
| Dimethyl benzyl carbinyl acetate | 5.0 | | |
| iso-Butyl benzoate | 5.0 | | |
| Neroli oil | 3.0 | | |
| | 100.0 | | |

Total amount of components—68.0
Number of components present—9
Average amount of each component—7.6
Number of classes represented—6

In this Example, the deodorant effectiveness of a roll-on lotion according to the invention was evaluated in terms of its odour reduction value in the following manner:

A standard quantity of 0.25 g of either the test or the control roll-on lotion product was applied to the axillae of the panel of human subjects. The axilliary odour was then judged by trained assessors and the odour scores using the 0 to 5 scale were recorded and subjected to statistical analysis to obtain average scores.

| Results of Odour Reduction Value Test 6 using Roll-on Lotion | Control lotion | Test lotion |
|---|---|---|
| Average scores | 2.39 | 0.40 |
| Odour reduction value | | 1.99 |

EXAMPLE 7

A propellant based aerosol deodorant was prepared by blending the following ingredients:

| | % by weight |
|---|---|
| Ethanol | to 100 |
| Trichloromonofluoromethane (Arcton 11) | 35 |
| Dichlorodifluoromethane (Arcton 12) | 35 |
| Deodorant Composition 6 | 0.5 |

A control aerosol product from which the deodorant composition had been omitted was also provided for comparison.

The deodorant composition was that described in Example 6.

In this example, the deodorant effectiveness of an aerosol deodorant according to the invention was evaluated in terms of its odour reduction value in the following manner:

A standard quantity of 0.5 g of either the test or the control aerosol deodorant product was applied to the axillae of the panel of human subjects. The axilliary odour was then judged by trained assessors and the odour scores using the 0 to 5 scale were recorded and subjected to statistical analysis to obtain average scores.

| Results of Odour Reduction Value Test 7 using Aerosol Deodorant | Control spray | Test spray |
|---|---|---|
| Average scores | 2.02 | 0.05 |
| Odour reduction value | | 1.97 |

The following products are illustrative of further products of the invention which comprise a vehicle, which can be a liquid or a solid, onto or into which a deodorant composition can be incorporated, included or deposited.

In the following Examples, the proportions of ingredients are in parts by weight:

Talcum powder

Zinc stearate—50
Light calcium carbonate—250
Talc—695
Deodorant composition—5

Deodorant Powder (for feet, etc.)

Zinc oxide—50
Zinc stearate—50
Chlorhexidine diacetate—3
Light calcium carbonate—100
Talc—794
Deodorant composition—3

Bath Salts

Sodium sesquicarbonate—84.5
Sodium perborate—5
Borax—10
Deodorant composition—0.5

Depilatory Cream

Strontium sulphide—300
Titanium dioxide—30
Zinc oxide—70
Calcium carbonate—50
Glycerin—80
Gum Tragacanth—50
Water—418
Deodorant composition—2

Body Lotion

Petrolium jelly—50
Mineral oil—400
Lanolin—25
Sorbitan sesquioleate—30
Beeswax—20
Zinc stearate—5
Borax—5
Water—443
Preservatives—22
Deodorant composition—5

Body Perfume

Carboxyvinyl polymer—3
Di-isopropyl adipate—20
Polyoxyethylene cholesterol—30
Alcohol—500
Polyoxyethylene oleyl ether—75
Triethanolamine—20
Water—344
Deodorant composition—8

Bath Oil

Isopropyl myristate—300
Diethyl phthalate—100
Mineral oil and colour—350
Deodorant composition—200

Sunscreen Oil

Homomenthyl salicylate—80
Mineral oil—917
Preservative—1
Deodorant composition—3

Aerosol Deodorants (i) Isopropyl myristate—0.6
Deodorant composition—0.65
Monochlorodifluoromethane—49.375
Dichlorodifluoromethane—49.375
(ii) Isopropyl myristate—0.6
Deodorant composition—0.65
Methylene chloride—25
Water—10
Hydrocarbon propellant (CAP 40)*—18
Industrial Methylated Spirit—45.75 (*Calor Aerosol Propellant Grade 40, which consists mainly of a mixture of propane and butanes).

The deodorant effectiveness of the foregoing Examples can be confirmed by a simple panel test in which a team of assessors is asked to record a score, on a 0 to 5 scale, for residual body malodour for each subject 5 hours after application of a deodorant skin treatment product according to the invention. This score is compared with that derived following the application to the skin of the corresponding control product from which the deodorant composition has been omitted.

This comparative panel test can be conducted in a manner similar to the Deodorant Value Test as hereinbefore described, the products, both test and control, being applied separately to the axillae of the panel of 50 subjects and the assessment subsequently being carried out 'blind' by a minimum of three assessors.

Deodorant Value of Deodorant Compositions 1 to 6

The deodorant value of each of the deodorant compositions illustrated in the foregoing Examples was determined by the Deodorant Value Test as described hereinbefore using the standard 80/20/5 soap base. The results were as follows:

| Deodorant composition | Average scores Control bar | Average scores Test bar | Deodorant value |
|---|---|---|---|
| 1 | 3.46 | 2.93 | 0.53 |
| 2 | 3.34 | 2.73 | 0.61 |
| 3 | 3.04 | 2.47 | 0.57 |
| 4 | 3.25 | 2.10 | 1.15 |
| 5 | 3.30 | 2.70 | 0.60 |
| 6 | 3.25 | 2.33 | 0.92 |

It can be seen from the above results that each of the deodorant compositions 1 to 6 had a deodorant value which was greater than 0.50 which defines the minimum deodorant value of a deodorant composition suitable for use in the deodorant detergent compositions of the invention.

APPENDIX

The following glossary provides further information, including the suppliers' names, which will aid identification of some of the aforementioned deodorant components and ingredients.

Dimyrcetol: Dimyrcetol (IFF)
Hercolyn D: Tetrahydro abietate + dihydro abietate (HP)
LRG 201: Oakmoss speciality (RB)
Pelargene: Pelargene (PPL)
Rose-D-Oxide: Rose oxide synthetic (PPL)
Sandalone: Sandalone (PPL)

Perfume Houses

HP: Hercules Powder Co.
IFF: International Flavour & Fragrances Inc.
RB: Roure Bertrand
PPL: Proprietary Perfumes Limited All materials which are classified by a name and number, such as those having the 'AB' notation, are obtainable from Proprietary Perfumes Limited.

What is claimed is:

1. A deodorant skin treatment product comprising:
    (i) from 0.01 to 20% by weight of a deodorant composition having a deodorant value of from 0.50 to 3.5 as measured by the Deodorant Value Test;
    (ii) up to 99.9% by weight of a cosmetically acceptable vehicle for the composition; the deodorant composition comprising from 45 to 100% by weight of deodorant components, said components having a lipoxidase-inhibiting capacity of at least 50% or a Raoult variance ratio of at least 1.1, said components being classified into six classes consisting of:
    Class 1: phenolic substances
    Class 2: essential oils, extracts, resins and synthetic oils
    Class 3: aldehydes and ketones
    Class 4: polycyclic compounds
    Class 5: esters
    Class 6: alcohols,
    provided that where a component can be classified into more than one class, it is placed in the lower or lowest numbered class;
    said components being so selected that
        (a) the deodorant composition contains at least five components of which at least one must be selected from each of class 1, class 2 and class 4;
        (b) the deodorant composition contains components from at least 4 of the 6 classes; and
        (c) any component present in the deodorant composition at a concentration of less than 0.5% by weight of said composition is eliminated from the requirements of (a) and (b).

2. The deodorant skin treatment product of claim 1 wherein the deodorant composition has a deodorant value of from 0.90 to 3.5 as measured by the Deodorant Value Test.

3. The deodorant skin treatment product of claim 1 wherein the deodorant composition has a deodorant value of from 1.20 to 3.5 as measured by the Deodorant Value Test.

4. The deodorant skin treatment product of claim 1 wherein the amount of deodorant components present in said class comprising phenolic substances and said class comprising essential oils, extracts, resins and synthetic oils and said class comprising polycyclic compounds, is at least 1% by weight of the deodorant composition for each of said classes, and the amount of deodorant components present in said further class chosen from the remaining three classes is at least 1% by weight of the deodorant composition.

5. The deodorant skin treatment product of claim 1 wherein the average concentration of all such components present is at least 5% by weight where four of said classes is represented, or at least 4.5% by weight where five or six of said classes is represented.

6. The deodorant skin treatment product of claim 1 wherein the amount of deodorant components present in said class comprising phenolic substances and said class comprising essential oils, extracts, resins and synthetic oils and said class comprising polycyclic compounds, is at least 3% by weight of the deodorant composition for each of said classes and the amount of deodorant components present in said further class chosen from the remaining three classes is at least 3% by weight of the deodorant composition.

7. The deodorant skin treatment product of claim 1 wherein at least five of the classes is represented.

8. The deodorant skin treatment product of claim 1 wherein all six classes are represented.

9. The deodorant skin treatment product of claim 1 wherein the vehicle comprises from 80–99.99% by weight of the product.

10. A process for preparing the deodorant skin treatment product of claim 1 which comprises mixing the deodorant composition with the cosmetically acceptable vehicle for the composition to provide a deodorant skin treatment product, said product comprising from 0.01 to 20% by weight of the deodorant composition and up to 99.99% by weight of the vehicle.

11. A method for suppressing human body malodour which comprises applying to the skin in the region of apocrine sweat glands the deodorant skin treatment product of claim 1.

12. The deodorant skin treatment product of claim 1 wherein the said deodorant components are chosen from:

Class 1—Phenolic substances
    iso-Amyl salicylate
    Benzyl salicylate
    Carvacrol
    Clove leaf oil
    Ethyl vanillin
    iso-Eugenol
    LRG201
    Mousse de chene Yugo
    Pimento leaf oil
    Thyme oil red Class 2—Essential Oils, extracts, resins, "synthetic" oils (denoted by "AB")
    Benzoin Siam resinoids
    Bergamot AB 37
    Bergamot AB 430
    Geranium AB 76
    Geranium oil
    Opoponax resinoid
    Patchouli oil
    Petitgrain oil
    Pomeransol AB 314

Class 3—Aldehydes and ketones
    6-Acetyl-1,1,3,4,4,6-hexamethyltetrahydronaphthalene
    p-t-Amyl cyclohexane
    p-t-Butyl-$\alpha$-methyl hydrocinnamic aldehyde
    2-n-Heptyl cyclopentanone
    $\alpha$-iso-Methyl ionone
    $\beta$-Methyl naphthyl ketone Class 4—Polycyclic compounds
    Coumarin
    1,3,4,6,7,8-Hexahydro-4,6,6,7,8,9-hexamethyl cyclopenta-$\gamma$-2-benzopyran
    3a-Methyl-dodecahydro-6,6,9a-trimethylnaphtho(2,1-b)furan
    $\beta$-Naphthyl methyl ether Class 5—Esters
    o-t-Butylcyclohexyl acetate
    p-t-Butylcyclohexyl acetate
    Diethyl phthalate
    Nonanediol-1,3-diacetate
    Nonanolide-1:4
    i-Nonyl acetate
    i-Nonyl formate Class 6—Alcohols
    Dimyrcetol
    Phenylethyl alcohol
    Tetrahydromuguol.

* * * * *